(12) United States Patent
St. Ville

(10) Patent No.: US 7,203,628 B1
(45) Date of Patent: Apr. 10, 2007

(54) MANUFACTURING SYSTEM AND METHOD

(76) Inventor: James A. St. Ville, 3908 E. Broadway Rd., Ste. 110, Phoenix, AZ (US) 85035

( * ) Notice: Subject to any disclaimer, the term of this patent is extended or adjusted under 35 U.S.C. 154(b) by 0 days.

(21) Appl. No.: 09/643,982

(22) Filed: Aug. 23, 2000

Related U.S. Application Data

(60) Provisional application No. 60/149,896, filed on Aug. 23, 1999.

(51) Int. Cl.
*G06F 17/50* (2006.01)

(52) U.S. Cl. .............. 703/1; 700/98; 264/219; 524/413

(58) Field of Classification Search ............ 700/98, 700/45, 97, 117, 118, 160, 182; 604/20, 604/8, 3; 703/2, 7, 1; 438/149, 158; 429/331; 428/141; 264/219; 606/60, 200; 435/198; 600/14, 3; 345/473; 524/413; 84/383; 623/23.61
See application file for complete search history.

(56) References Cited

U.S. PATENT DOCUMENTS

| | | | |
|---|---|---|---|
| 4,819,161 A | | 4/1989 | Konno et al. ............. 700/86 |
| 4,889,526 A | * | 12/1989 | Rauscher et al. ............ 600/14 |
| 4,909,127 A | | 3/1990 | Skelton et al. .............. 87/33 |
| 4,936,862 A | | 6/1990 | Walker et al. .......... 364/468 X |
| 4,975,262 A | | 12/1990 | Suto et al. .............. 423/447.1 |
| 5,023,800 A | | 6/1991 | Carver et al. .......... 364/474.24 |
| 5,098,621 A | * | 3/1992 | Hermann ................ 264/46.4 |
| 5,351,196 A | | 9/1994 | Sowar et al. .......... 364/468 X |
| 5,397,365 A | | 3/1995 | Trentacosta .............. 623/18.11 |
| 5,487,012 A | | 1/1996 | Topholm et al. ........ 364/468 X |
| 5,552,995 A | | 9/1996 | Sebastian ................. 700/97 |
| 5,563,199 A | * | 10/1996 | Harada et al. ............. 524/413 |

(Continued)

FOREIGN PATENT DOCUMENTS

GB   2 311 154 A   9/1997

(Continued)

OTHER PUBLICATIONS

St. Ville, et al., *The Anatomy of Midthigh Pain After Total Hip Arthroplasty*, Johns Hopkins APL Technical Digest, Apr.-Jun. 1991, vol. 12, No. 2, pp. 198-212.

(Continued)

*Primary Examiner*—Paul Rodriguez
*Assistant Examiner*—Kandasamy Thangavelu
(74) *Attorney, Agent, or Firm*—Nixon & Vanderhye, PC

(57) ABSTRACT

A method for manufacturing an object having a potential $\{x\}$ that is generated in response to a field $\{f\}$ applied thereto. A computerized mathematical model of the object is generated by discretizing a geometric model of the object into a plurality of finite elements and specifying values for the field $\{f\}$ and potential $\{x\}$ relative to the finite elements. The material properties of the finite elements are specified to have a particular symmetry and a material property matrix $[k]$ is calculated based on the relationship $\{f\}=[k]\{x\}$ and the specified symmetry. Material property coefficients are extracted from the material property matrix $[k]$ for each finite element in the computerized mathematical model and the extracted material property coefficients are compared to material property coefficients for known materials to match the extracted material property coefficients to the material property coefficients for known materials. Manufacturing parameters for controlling manufacturing equipment are determined based on the matched material property coefficients and the manufacturing equipment is controlled in accordance with the determined manufacturing parameters to thereby manufacture the object.

38 Claims, 9 Drawing Sheets

U.S. PATENT DOCUMENTS

| | | | |
|---|---|---|---|
| 5,581,489 A | 12/1996 | Groothuis et al. | 364/578 |
| 5,594,651 A * | 1/1997 | St. Ville | 700/98 |
| 5,634,214 A | 6/1997 | St. Ville | 2/161.2 |
| 5,654,077 A * | 8/1997 | Wu et al. | 428/141 |
| 5,683,243 A | 11/1997 | Andreiko et al. | 433/3 |
| 5,796,617 A * | 8/1998 | St. Ville | 700/98 |
| 5,822,206 A | 10/1998 | Sebastian et al. | 364/468.03 |
| 5,824,085 A | 10/1998 | Sahay et al. | 128/898 |
| 5,942,496 A * | 8/1999 | Bonadio et al. | 514/44 |
| 6,015,289 A | 1/2000 | Andreiko et al. | 433/3 |
| 6,087,571 A * | 7/2000 | Legere | 84/383 |
| 6,121,033 A * | 9/2000 | Tadros et al. | 435/198 |
| 6,126,659 A * | 10/2000 | Wack | 606/60 |
| 6,197,624 B1 * | 3/2001 | Yamazaki | 438/158 |
| 6,231,590 B1 * | 5/2001 | Slaikeu et al. | 606/200 |
| 6,248,057 B1 * | 6/2001 | Mavity et al. | 600/3 |
| 6,263,252 B1 * | 7/2001 | St. Ville | 700/98 |
| 6,289,242 B1 * | 9/2001 | Phipps et al. | 604/20 |
| 6,290,889 B1 * | 9/2001 | Castanie et al. | 264/219 |
| 6,296,667 B1 * | 10/2001 | Johnson et al. | 623/23.61 |
| 6,348,042 B1 * | 2/2002 | Warren, Jr. | 604/8 |
| 6,372,558 B1 * | 4/2002 | Yamanaka et al. | 438/149 |
| 6,456,289 B1 * | 9/2002 | O'Brien et al. | 345/473 |
| 2002/0009651 A1 * | 1/2002 | Barker et al. | 429/331 |

FOREIGN PATENT DOCUMENTS

| | | | |
|---|---|---|---|
| WO | | 91/04544 | 4/1991 |
| WO | WO 97/18842 | * | 5/1997 |
| WO | | 97/30652 | 8/1997 |

OTHER PUBLICATIONS

*Software for Analysis and Design,* Machine Design-Basics of Design Engineering, Cleveland, Ohio, No. 12, Jun. 1992, pp. 775, 776, 781, 782, 784, 786, 788, 790, 798, 800 and 804.

Taylor, *Computational Problems in Orthopaedic Biomechanics,* Electronic Packaging Materials Science VII Symposium, Boston, MA, Nov.-Dec. 1993, pp. 221-231.

Encyclopaedic Dictionary of Physics, Ed. J. Thelwis, Pergamon Press 1961.

Mc Clintock F. and Argon A.: "Mechanical Behaviour of Materials", Addison-Wesley, USA, (1968), Chapter 3.

* cited by examiner

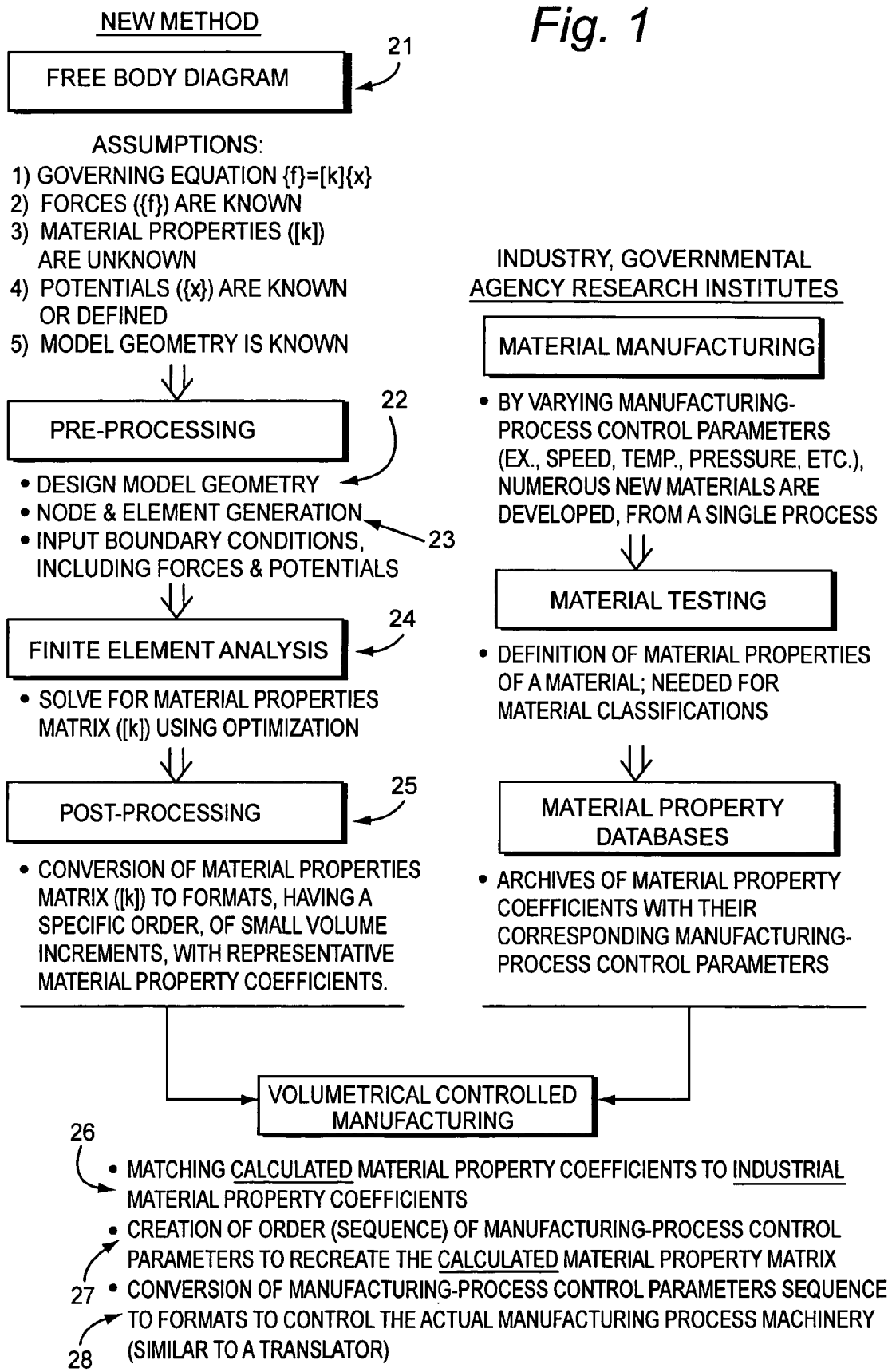

| | INTACT FEMUR |
|---|---|
| A | 0.221 ± 0.057 |
| B | 0.875 ± 0.119 |
| C | 0.698 ± 0.122 |
| D | 1.217 ± 0.150 |
| E | 1.315 ± 0.131 |
| F | 1.208 ± 0.131 |

| M1-1 | E1-1 | σ1-1 | PROCESS | PROCESS PARAMETERS |
|------|------|------|---------|--------------------|
| M1-2 | E1-2 | σ1-2 | PROCESS | PROCESS PARAMETERS |
| ⋮ | ⋮ | ⋮ | ⋮ | ⋮ |
| M1-n | E1-n | σ1-n | PROCESS | PROCESS PARAMETERS |

| M2-1 | σ'2-1 | PROCESS | PROCESS PARAMETERS |
|------|-------|---------|--------------------|
| M2-2 | σ'2-2 | PROCESS | PROCESS PARAMETERS |
| ⋮ | ⋮ | ⋮ | ⋮ |
| M2-n | σ'2-1 | PROCESS | PROCESS PARAMETERS |

MANUFACTURING SYSTEM AND METHOD

RELATED APPLICATION

This application claims priority from provisional Application No. 60/149,896, filed on Aug. 23, 1999, the contents of which are incorporated herein by reference.

TECHNICAL FIELD

The present invention generally relates to articles of manufacture and, more particularly, to a method and apparatus for manufacturing objects having response characteristics that are optimized for a desired application or use.

BACKGROUND AND SUMMARY OF THE INVENTION

Historically, analysis performed by engineers is one step in the long process in the attempt to simulate and verify real-world expected performance of engineered products. Complete models containing information such as geometry, material properties, loads and analysis type are entered into an analysis program and basic results such as displacements are calculated. These values can then be compared to predetermined limits of the material, whether isotropic, orthotropic, or anisotropic, to locate any critical areas in the model. Areas of the model that exceed any specified limit need to be reconfigured to obtain positive margins of safety, although a majority of the time, areas of high margin of safety are left unchanged or not optimized. Iterations such as changing the material or component geometry can reduce the margin of safety. This process is both lengthy and not very cost effective.

A method known as Volumetrically Controlled Manufacturing (VCM) can assist in reducing cost, time to manufacturing, and margins of safety. VCM is described in U.S. Pat. Nos. 5,796,617 and 5,594,651, the contents of which are incorporated herein. VCM may be applied, for example, to an orthopedic procedure known as THA (Total Hip Anthroplasty). This procedure involves replacing a patient's hip with a hip stem so as to maintain the patient's physiological capability of normal walking motion. Traditional analysis revealed a couple of areas of high stresses that an isotropic material displaced onto surrounding bone and caused pain in the patient and premature failure of that same bone structure, prompting post-THA surgery. The problem that arose involved using a configuration and material that was much stiffer than what it replaced. Attempts at reducing the stiffness involved using composite materials. These attempts however failed due to inter-laminar shear causing delamination, and secondarily matrix/fiber disbonding. These failures occurred due to an inability to come up with a ply configuration that could withstand the load environment and unique structural properties of bone.

In order to provide an efficient analysis tool to determine the optimum material properties for an engineered product such as a hip stem, a different approach from traditional analysis had to be made. The VCM process encompasses this new approach. Instead of determining the displacements, stresses and strains in a product using traditional analysis methods, through real world testing, displacements are recorded and entered into the analysis. The material properties are now the unknowns and are solved for.

As described in greater detail below the material properties may be solved for in an iterative analysis process. The analysis continues until specified elements display displacements all within a specified tolerance. In this way, an iteration process continues until convergence, thereby, optimizing the entire model for its particular environment and loading condition. This plays very much into the use of composite materials because they can be tailored in many different ways to come up with the desired material property, unlike isotropic metallics that have less tailorability in comparison to composites.

The optimization may also be extended to control the type of solutions that result from the above-described processing. For example, the system may be constrained to find a solution in which the finite volume elements ("voxels") that make up the object have certain symmetries. By way of illustration, the system may be constrained to find a solution in which the voxels are isotropic or are transversely isotropic. Imposing such symmetries on the solutions improves manufacturability by defining each voxel in terms of properties (e.g., Poisson's ratio, Young's modulus) that are the same, or that have certain symmetries, throughout the voxel. In some implementations, the system may be configured to generate solutions for isotropic voxels, transversely isotropic voxels, and for anisotropic voxels. The actual solution used for manufacturing may be chosen based on the relative ease of controlling manufacturing equipment to produce the desired object.

As mentioned above, composite materials are useful for VCM because they can be tailored in many different ways to come up with the desired material property. A composite material is a combination of two or more materials in which the individual materials remain separate on a macroscopic level. One way to construct a composite material is to laminate structural fibers in appropriate matrices compatible with these fibers. As described in greater detail below, the matrices in which the fibers are incorporated may be modified to include certain "impurities". In the case of a THA, for example, the impurities may be biologic material, bone, crushed bone, co-factors, biological cells, bio-active materials, medications, antibiotics, radioactive materials, etc.

BRIEF DESCRIPTION OF THE DRAWINGS

These and other features and advantages provided by the invention will be better and more completely understood by referring to the following detailed description of presently preferred embodiments in conjunction with the drawings of which:

FIG. 1 illustrates the methodology for manufacturing an object in accordance with the present invention;

DETAILED DESCRIPTION OF EXAMPLE EMBODIMENTS OF THE INVENTION

Figure 2A:
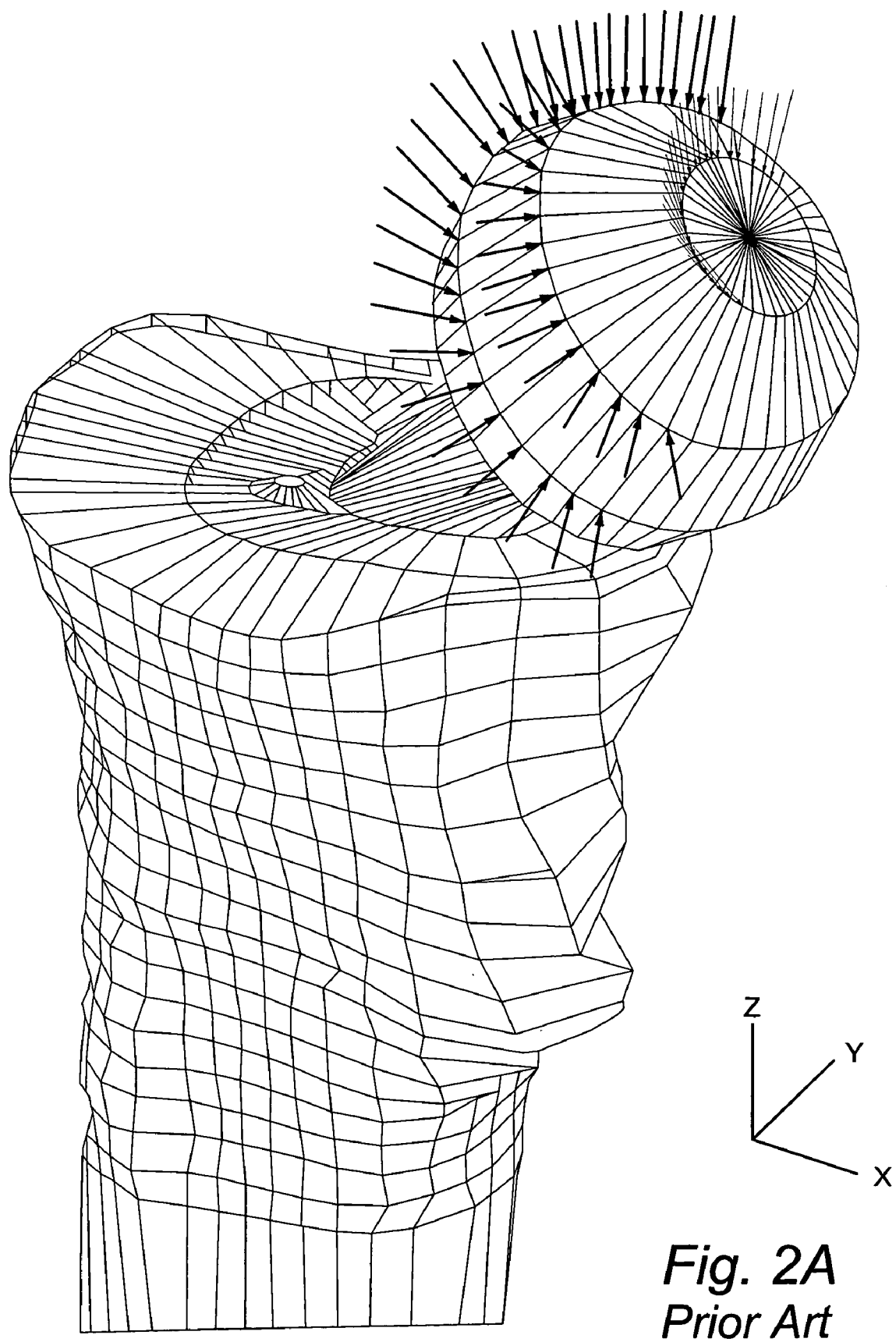
FIGS. 2A and 2B illustrates forces applied to the femoral head of a hip during a one-leg stance and rising from a chair, respectively.

FIG. 1 will be used to describe a methodology for manufacturing an object or part in accordance with the present invention. As will become apparent from the description below, object or part (hereinafter "object") as used herein refers to any object that may be manufactured by a process or technique in which manufacturing parameters may be controlled to vary constitutive or material properties within the object. The methodology for manufacturing an object in accordance with the instant invention is based on solutions of the equation $$\{f\}=[k]\{x\}$$

where $\{f\}$ represents a field that will be applied to the object in its intended use, $\{x\}$ represents a potential corresponding to the applied field, and $[k]$ represents the material properties of the object.

The methodology of the instant invention may be utilized with any manufacturing technique in which the manufacturing parameters may be varied. For example, a braiding process using a braider may be used to manufacture fiber composite objects. Fiber composite materials are finding increasing use as the construction material for components such as body panels of automobiles, aircraft, prosthetic implants, golf club shafts, tennis rackets, bicycle frames, and fishing poles. These composite materials offer high strength equal to, or exceeding, that of metallic materials, for example, while at the same time are lighter in weight and have other improved functional properties. Parameters such as the speed of the braider bed and/or mandrel, the thickness of the fibers, and the tension applied to the fibers are controlled to vary the stiffness properties of the fiber composite material. An example of a braider bed designed for controlled braiding of composite materials is shown in U.S. Pat. No. 4,909,127 to Skelton. Three-dimension woven fabrics are also discussed in U.S. Pat. No. 4,975,262 to Suto.

Composite materials may also be constructed by laminating structural fibers in appropriate matrices compatible with these fibers as described in U.S. Pat. No. 5,023,800 to Carver et al. Fiberglass is a widely used composite system that incorporates glass fibers within an epoxy resin matrix. For formation of aircraft components, more exotic composite systems having improved properties are desirable. Currently available for use are exotic inorganic materials such as carbon fibers, boron fibers, improved glass fibers, aluminum oxide fibers, inorganic whiskers of different materials and certain organic fibers such as aramides and extended chain polyethylenes. These fibers or whiskers are incorporated as threads, fabrics, mats, or the like in appropriate resins, as for instance thermosetting epoxies, polyesters, polyethers, polyimides, and bismaleimides or thermoplastic polyamideimines, polyether sulfones, polyether ketones, polyphenylene sulfides and other similar polymeric materials. Composite objects may be formed utilizing molding techniques—using either external molds that are of a complementary shape to an object or an internal mandrel type mold on which the composite object is built. A mold utilized for the formation and curing of a composite object is called a bonding tool and the curing is carried out under precisely controlled temperatures and pressures.

In accordance with one aspect of the present invention, certain "impurities" may be introduced into the matrices in which the fibers are incorporated. In the case of a THA, for example, the impurities may be biologic material, bone, crushed bone, co-factors, biological cells, bio-active materials, medications, antibiotics, radioactive materials, and the like. VCM provides manufacturing on an element-by-element basis and the outer surface elements can be made to include in the matrix material a certain percentage of the above-mentioned impurities. The actual percentage may vary with depth from the surface (e.g., as the surface is approached, the concentration may be increased). By incorporating, for example, biological material in a THA, biological growth to the implant itself can be stimulated. If medication or antibiotics are incorporated in the THA, the medication can diffuse out into the surrounding tissues.

A contouring process using a contouring system on a lathe or a milling machine may be used to manufacture metal objects. Contouring refers to the continuous removal of material in an application such as turbine-blade machining. Parameters such as the part surface, the drive surface, and the check surface may be controlled to vary the milling tool path and thus the contouring. Part surface refers to the surface on which the end of the milling tool is riding; drive surface refers to the surface against which the edge of the milling tool rides; and check surface refers to a surface at which the current milling tool motion is to stop. Details of a contouring system are shown in Bedworth et al., Computer-Integrated Design and Manufacturing, McGraw-Hill Inc. (1991).

Of course, the instant invention is not limited to objects formed using braiding, molding, or contouring and the above discussions are merely examples of manufacturing techniques which may be utilized in the inventive methodology. Other processes and techniques include by way of example, but not by way of limitation, polymer manufacturing processes, crystallization techniques, ceramic manufacturing techniques, and the like.

At step 21, the field(s) $\{f\}$ that will be applied to the object in its intended use, as well as the desired potential(s) or response(s) $\{x\}$ to these field(s), are defined. For example, an object may be applied with a mechanical force field, an electric current field, a magnetic field, a thermal flux field, and/or a fluid velocity field. Other fields $\{f\}$ may be derived using these primary fields. For example, an acoustic field may be derived by combining the mechanical force field and the fluid velocity field. A magnetohydrodynamics field may be derived by combining the fluid velocity field and the magnetic field. Each of the above-identified fields has a corresponding potential. These potentials are displacement, corresponding to the mechanical force field; voltage, corresponding to the electric field; magnetic vector potential, corresponding to the magnetic field; temperature, corresponding to the thermal flux field; and fluid potential, corresponding to the fluid velocity field.

Figure 2B:
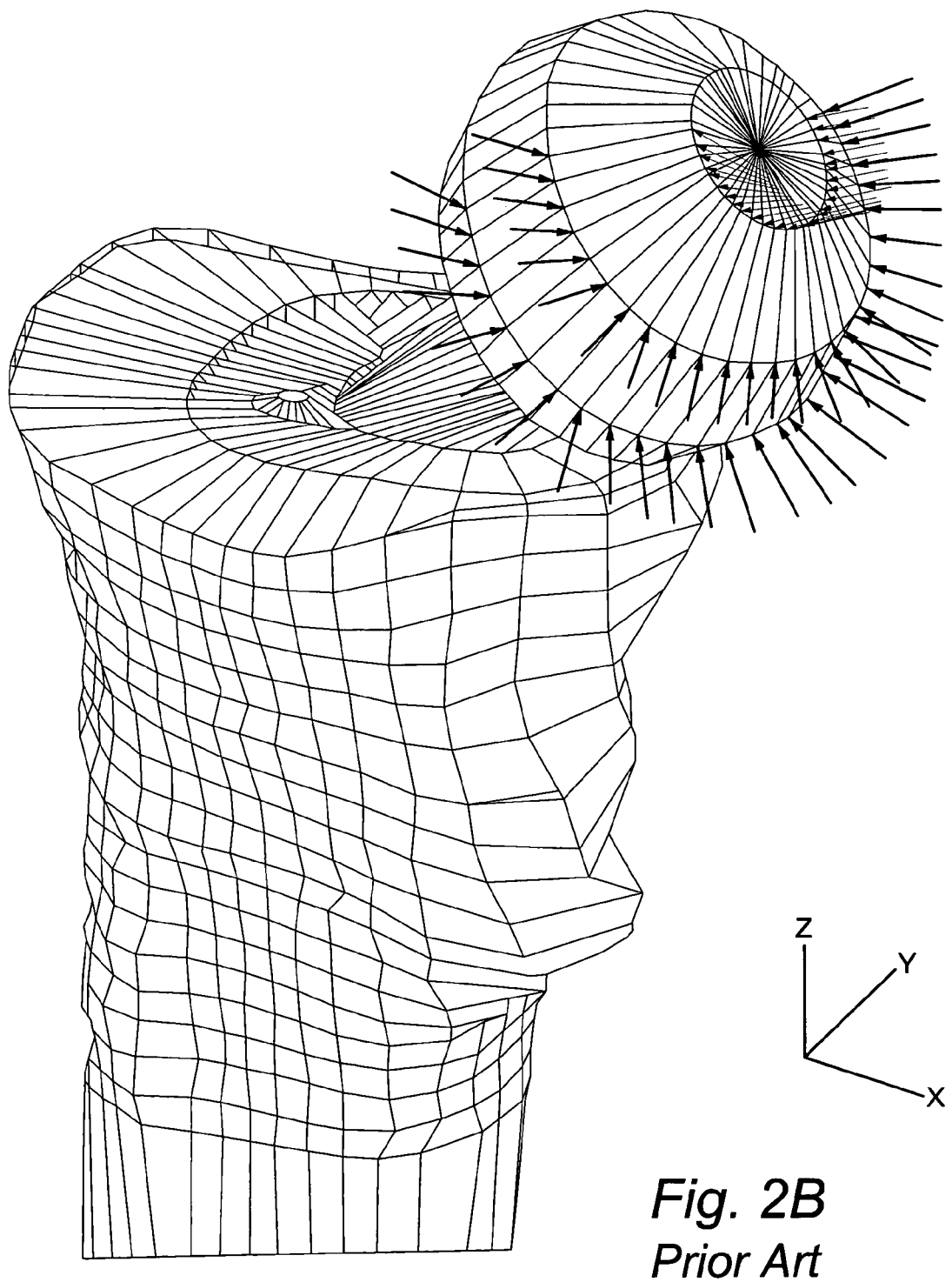

As noted, the fields defined at step 21 represent one or more fields that will be applied to the object in its intended use. For example, in the case of a prosthetic hip, the field may be the mechanical forces that will be applied to the prosthetic hip after implant in the human body. For example, the arrows in FIGS. 2A and 2B represent the forces (direction and magnitude) applied to the femoral head during a one-leg stance (during walking, for example) and rising from a chair, respectively. The force distributions and orientations are based on in vivo studies reported at, for example, Hodge et al., "Contact Pressures in the Human Hip Joint Measured In Vivo," Proc. Natl. Acad. Sci. U.S.A., 83, 2879–2883 (1986). The resultant force of each of these forces was approximately 2000 Newtons (N), with an orientation change from one-leg stance to midrise loading. As another example, in the case of a heat conduction element, the field may be the thermal flux that will be applied to the object in its intended use. Of course, an object may be applied with more than one field and each of these fields may be defined at step 21. For example, an electrical conductor may be applied with an electric field, a magnetic field, and a mechanical force field in its intended use.

Figures 3A, 3B:
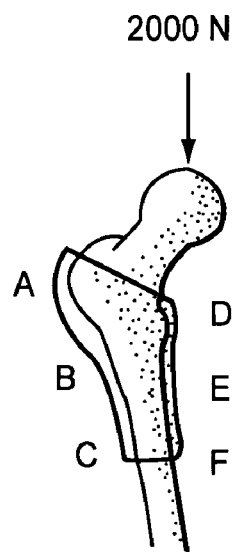
FIGS. 3A and 3B illustrate a force applied to an in vivo hip and the resultant stresses, respectively.

The potential(s) {x} defined at step 21 define the manner in which the manufacturer desires the object to respond when the defined field or fields {f} are applied thereto. In the case of the prosthetic hip, the defined potentials are the desired displacements (which correlate mathematically to the stresses) in the prosthetic hip when the prosthetic hip is subjected to the mechanical forces shown in FIGS. 2A and 2B during walking and rising from a chair. If the manufacturer desires the prosthetic hip to respond to forces in the same manner as an in vivo hip, the "desired displacements" in the prosthetic hip may, for example, correspond to the displacements generated in an in vivo hip during walking and rising from a chair. FIG. 3A illustrates an in vivo hip applied with a force of 2000N as indicated and FIG. 3B is a table setting forth measurements of the displacements generated at the points labeled A, B, C, D, E, and F in FIG. 3A in response to this applied force. Thus, a manufacturer desiring to manufacture a prosthetic hip which responds to the force indicated in FIG. 3A in the same manner as an in vivo hip would define the force {f} to be the force indicated in FIG. 3A and would define the displacements {x} to be the displacements set forth in the table of FIG. 3B. Similarly, in the case of the heat conduction element that is applied with a thermal flux field, the defined responses correspond to desired temperatures at various portions of the heat conduction element when the defined thermal flux field is applied. In the case of an electrical conductor which is applied with an electric field, a magnetic field, and a mechanical force field, the defined responses correspond to desired displacements at various portions of the conductor when the defined mechanical force field is applied, to desired magnetic vector potentials at various portions of the conductor when the defined magnetic field is applied, and to desired voltages at various portions of the conductor when the defined electric field is applied, respectively.

At step 22, computer aided design is used to geometrically model the object to be manufactured. Geometric modeling is a technique of using computational geometry to define geometric objects. The purposes of geometric modeling are object representation, which mandates a complete definition of the object for manufacturing and other applications such as finite element analysis; design, which allows the user to input and manipulate a geometric specification of the object; and rendering, which uses the geometry to paint a realistic picture of the object on a computer graphics output device. The initial geometric model of the object or part may, for example, be based on the experience of the design engineer or be dictated by the intended use of the object or part. For example, the initial geometric model of a prosthetic hip is based on an in vivo hip. Of course, this initial geometric model may be subsequently modified for adaptation to an individual of a particular height and/or weight. The initial design geometry of a golf club shaft is again known, i.e., a cylinder of predetermined length and diameter. Again, this initial design geometry may be modified to provide a shaft for a golfer of a particular height or to provide a shaft having a diameter that varies, e.g., a narrower diameter near the club head. Suitable CAD software packages for carrying out this geometric modeling include I-DEAS, CATIA, and ANVIL-5000. These software packages may be run, for example, on UNIX-based work stations such as those available from Sun Microsystems or Silicon Graphics. Of course, the choice of computer will be determined by the computational power required and the invention is not limited in this respect. The use of such computer aided design software packages permits a geometric model of an object or part to be defined by a user and modified quickly and results in generation of geometry data which can be converted to formats useful in a computer aided manufacturing step and/or to formats useful a finite element method step, which steps are discussed in greater detail below. It is noted that the initial geometric model can be image data generated by scanning an object having the desired geometry. For example, the initial geometric model in the case of a prosthetic hip can be generated by X-raying a cadaveric hip using, for example, a Siemens Somatom DR3 or a GE 9800 CT scanner. This image data may be converted to a format usable by the CAD software package or may be directly converted to a format usable by a finite element software package (for example, a PATRAN format) to be described below.

At step 23, a finite element model of the object is generated using the finite element method. The finite element method is based on the theory that an irregularly shaped object can be divided into smaller regular finite elements. Each element can then be treated separately and the aggregate effect is the sum of the effects of all of the finite elements in the object. The finite element model is created by a user using an appropriate software package that operates on the geometric model developed in step 22. Thus, the finite element software package generally accesses a data file that contains the geometry of the object developed in step 21. Some integrated software packages, such as I-DEAS from SDRC, Inc., link modules for geometric modeling and finite element analysis so that the user does not have to redefine the geometry specifically for finite element analysis. Other suitable software packages for generating the finite element model include NASTRAN, ABAQUS, and ANSYS.

Figure 4:
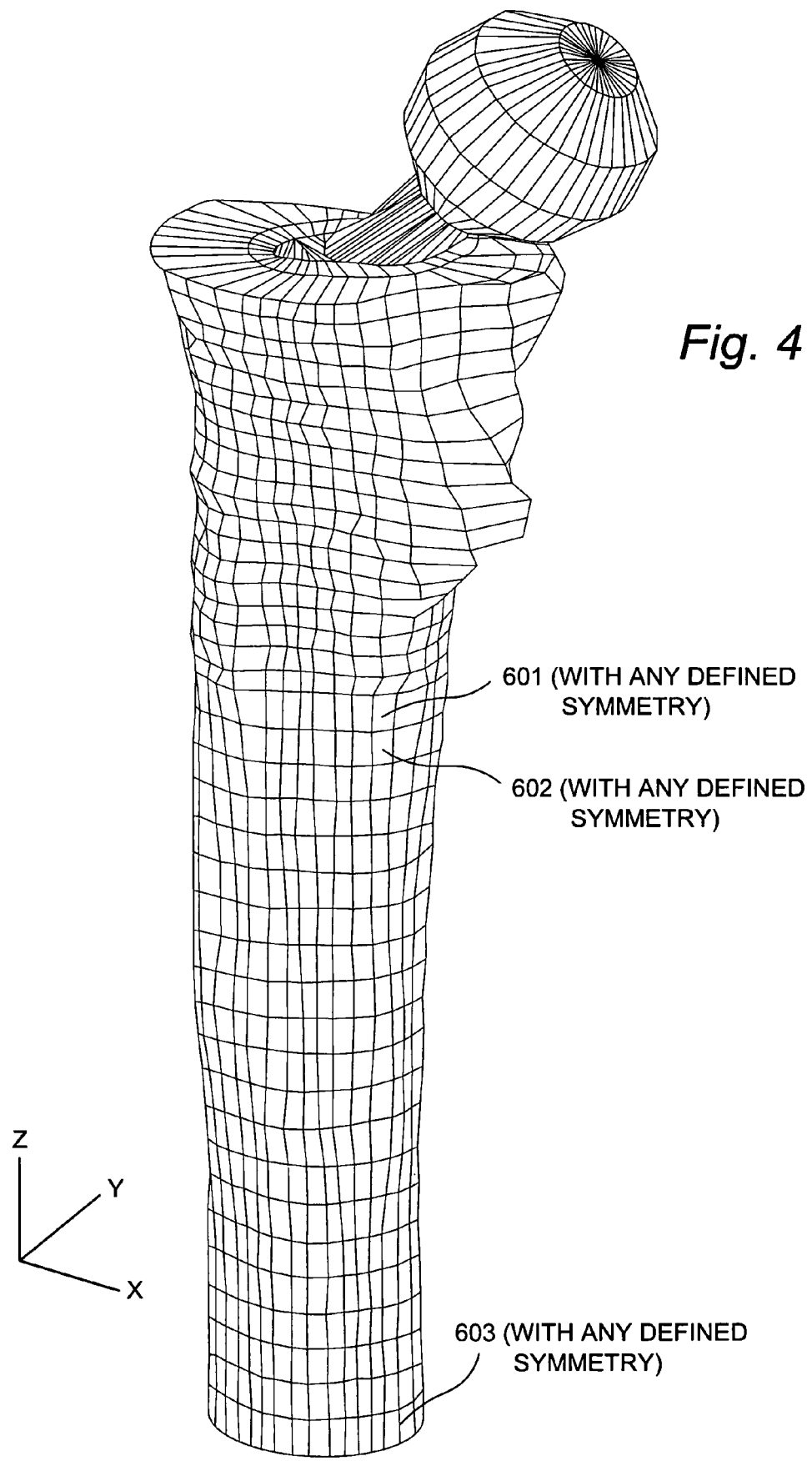
FIG. 4 illustrates a finite element model of a prosthetic hip.

Thus, the finite element model is generated by dividing the geometric model of the object into a plurality of elements and then defining nodes at the boundaries of the elements. An exemplary finite element model for a prosthetic hip is shown in FIG. 4. A variety of element shapes may be used in the finite element model of the object. The number and types of elements selected are generally based on the type of field and the geometry of the object. The various finite element software packages identified above generally include libraries of elements and element clusters to enable modeling of areas having particular geometries with a user-specified degree of accuracy. Thus, an element having a element size of a predetermined value or an element cluster of variable elements having a cluster size of the predetermined value may be utilize. If element clusters are utilized, the cluster may be repeated throughout the finite element model. A cluster may include elements that have different shapes. For example, if the object to be manufactured will be subject to shear forces, elements having shapes that are best suited for modeling shear forces may be utilized and oriented as appropriate. When these elements are grouped together, they may define a cluster that may be repeated, for example, in areas having similar geometries and/or which are applied with similar forces. In addition, different size elements may be used to model object portions of critical tolerance. So-called super-elements may be used where tolerance is not critical. Since the methodology of the invention is typically an iterative process as will be discussed below, if, for example, it is determined in a first iteration that there are one or more portions of the object where the nodal values do not change much, for computational purposes, a second later iteration may generate a finite element model of the object that includes one or more super-elements in these areas in order to simplify subsequent calculations.

The finite element model is completed by specifying the values and/or directions of the above-described fields {f} and potentials {x} at the nodes of the discretized object. In addition, any appropriate boundary conditions are imposed.

At step 24, the finite element software package is programmed to solve for the material properly matrix [k] using the relationship {f}=[k] {x}. That is,

[k]{x}={f}

[k]{x}{x}$^{-1}$={x}$^{-1}${f}

[k]={x}$^{-1}${f}

Because the field {f} and the potential {x} have been defined at step 21, the material property matrix [k] may be calculated. When {f} is the mechanical force field and {x} is the displacement, [k] is the stiffness matrix. When {f} is the thermal flux field and {x} is the temperature, [k] is the thermal conductivity. When {f} is the magnetic field and {x} is the magnetic vector potential, [k] is the magnetic reluctivity. When {f} is an electric current field and {x} is the voltage, [k] is electrical conductivity. The calculation of the matrix [k] at step 24 when the fields and potentials have been defined as described at steps 21 determines the optimum or near-optimum material property matrix for permitting a manufacturer to manufacture an object having desired responses for a specific application, i.e., for a specific application of forces.

The software for generating the solution to the equation may include an optimizer, a standard Non-Linear Finite Element Analysis (FEA) code, and a controller for controlling data flow between the optimizer and the FEA code. Once analysis has been performed by the FEA code, the controller sends the data to the optimizer to compare the resulting data from the analysis with the desired model parameters and tolerances. If any of the results are not within the desired tolerance range, selected parameters are conditioned by the optimizer, and the controller then sends the reconditioned data back to the FEA code for another analysis run. This process is continued until all user specified parameters in the model fall within the tolerance range, thus establishing convergence.

Optimization methodology may be provided for back-calculating the material properties so that the displacements at select nodes in the finite element model are as close as possible to the input target displacements. Such a problem is referred to as an inverse problem. The target displacements are usually obtained from experiments. A methodology must then, given the finite element (FE) model, be able to adjust the material properties systematically so that the computed (analytical) displacements are as close to the experimental displacements as possible.

Nonlinear programming (NLP) techniques may be used to solve the problem. Consider the optimal design problem as stated below:

Find $(x_i, i=1, \ldots, n)$
to minimize $f(x)=(D_j^E-D_j^A)^2 j=1, \ldots, n$
$g_k(x)=s_k \leq s_k^a, k=1, \ldots, m$
subject to $x_i^L \leq x_i \leq x_i^U$ where,
$x_i$ $i^{th}$ design variable (e.g. Modulus of elasticity Poisson's ratio, etc.)
$D_j^A$ displacement computed from FE model
$D_j^E$ target displacements (e.g. experimentally obtained)
$s_k$ stress invariant (e.g. von Mises) computed from the FE model
$s_k^a$ allowable (maximum) stress value
$x_i^L$ lower limit on the design variable
$x_i^U$ upper limit on the design variable The best solution to the optimal design problem (if one exists) is when the objective function f(x) is zero while all the constraints gk(x) are satisfied. With (a) noise in the input data, (b) limitations of the FE analysis, and (c) limitations of the numerical optimization technique, this theoretical zero-objective function generally cannot be obtained. However, the methodology can take the solution close to this theoretical solution.

The Feasible Directions Method (a well-known NLP technique) may be implemented and used as an optimizer software system. A non-linear FE computer program is used to solve the finite element model. The controller is used to read the problem input data and manage the optimizer and non-linear FEA computer program.

The optimizer may also be used to control the type of solution that results from the above-described processing. For example, the system may be constrained to find a solution in which the finite volume elements ("voxels") have certain symmetries. For example, the system may be constrained to find a solution in which the voxels are isotropic or are transversely isotropic. Bone, for example, is transversely isotropic. Imposing such symmetries on the solutions improves manufacturability by defining each voxel in terms of properties (e.g., Poisson's ratio, Young's modulus) that are the same, or have certain symmetries, throughout the voxel. In some implementations, the system may be configured to generate solutions for isotropic voxels, transversely isotropic voxels, and for anistropic voxels. The actual solution used for manufacturing may be chosen based on the relative ease of controlling manufacturing equipment to produce the desired object.

At step 25, the finite element software package is used to extract the material property coefficients for each of the elements in the finite element model from the material property matrix [k]. Specifically, the material property matrix [k] that is calculated at step 24 is the global or assembled material property matrix [k]. The material property coefficients for a particular element of the finite element model may be extracted from such a global or assembled matrix using a boolean locating function or some other locating function. For example, with reference to FIG. 4, the material property coefficients for element 601 are extracted, followed by the material property coefficients for element 602, etc. This procedure is repeated for each element in the model in order to generate a data sequence representing the material properties of the prosthetic hip at small volume increments.

Figure 5A:
FIGS. 5A and 5B illustrate material properties databases.
Figure 5B:

At step 26, the extracted material property coefficients are compared with known material property coefficients in a material property database or databases. FIG. 5A illustrates one organization of a material database 700. Material property data base 700 characterizes a plurality of materials M1-1, M1-2, . . . , M1-n by the values of stiffness properties such as Young's modulus (E) and Poisson's ratio (σ). For example, material M1-1 may be aluminum having a Young's modulus of 7.2×10$^{10}$ Pa and a Poisson's ratio of 0.32. Material M1-2 may be aluminum having a Young's modulus of $6.9 \times 10^{10}$ Pa and a Poisson's ratio of 0.35. Material M1-n may be cast iron having a Young's modulus of $8.8 \times 10^{10}$ Pa and a Poisson's ratio of 0.30. Of course, the invention is not limited to these specific materials. Respectively associated with each of these materials M1-1, M1-2, . . . , M1-n are a manufacturing process and the specific parameters of that process (such as temperature, pressure, etc.) that will produce the material with the corresponding stiffness properties. Similarly, as shown with reference to FIG. 5B, a material property data base 701 may characterize a plurality of materials M2-1, N2-2, . . . , M2-n by the values of electrical conductivity ($\sigma'$). Again, respectively associated with each of these materials M2-1, . . . , M2-n are a manufacturing process and the specific parameters of that process that will produce the material with the corresponding electrical conductivity. Similar material databases may be used to characterize materials by their thermal conductivity or magnetic reluctivity and to identify the manufacturing method and manufacturing parameters associated with each material.

Thus, the material property databases are archives of material property coefficients with their corresponding manufacturing process and manufacturing-process control parameters. Such databases are created and maintained by industrial manufacturers, government agencies, and research institutes. For example, when a material such as a metal, a plastic, or a composite is created using a particular manufacturing process, its properties may be determined through standard testing methods such as ASTM testing methods. When these properties have been determined, the set of manufacturing parameters such as temperature, pressure, etc. that was used to create the material having these properties is correlated to the material in order that the material may be reproduced in the future.

The comparison at step 26 between the extracted material property coefficients and the material properties data base is used to determine which material in the database has material properties which match or most closely match the properties corresponding to the extracted material property coefficients. Thus, referring to FIG. 4, the comparison will result in the identification of a first set of manufacturing parameters which will produce the portion of the prosthetic hip corresponding to element 601 with the desired stiffness properties; the identification of a second set of manufacturing parameters which will produce the portion of the prosthetic hip corresponding to element 602; etc. The above-described comparisons may be carried out, for example, using a knowledge base having a fact base for storing the extracted material property coefficient data for each of the elements (e.g., elements 601, 602, etc. of FIG. 4) and the material property data from the material data base, and a rule base containing rules for comparing and matching the extracted material property data for each of the elements and the material property data from the material data base. The level of matching (e.g., a perfect match, a close match) is application specific and is related, inter alia, to how much tolerance is permitted. If the object to be manufactured is a critical component, a very close or perfect match is desirable. If the object to be manufactured is a non-critical component, the matching criteria may be relaxed. Other criteria such as cost and the available manufacturing equipment may also determine the level of matching. Thus, by performing step 26, the sets of manufacturing-process control parameters for each and every portion of object are determined.

At step 27, the determined sets of manufacturing-process control parameters are ordered or sequenced to define the manufacturing-process controls that are necessary to manufacture the object. The manufacturing control parameters may be used to implement numerical control of the manufacturing equipment used to manufacture the object. Numerical control refers to the use of coded numerical information in the automatic control of manufacturing equipment. For machine tools, this might refer to the motion of the cutting tool or the movement of the part being formed against a rotating tool. The process of laying composite material to form lightweight alternatives to machined metal parts may also be implemented using numerical control. The necessary geometry and motion statements for manufacturing the object may then be programmed using a general purpose numerical control language to develop manufacturing control data. One such language is APT-AC Numerical Control Processor Program (available from IBM Corporation, Armonk, N.Y.). The APT-AC processor is a computer application program that accepts as input user-oriented language statements that describe the numerical control operations to be performed. A postprocessor may further process the manufacturing control data to tailor the information to a specific manufacturing process. At step 28, the post-processed data is supplied to a computerized manufacturing device that uses the supplied data to control the manufacturing of the object. The data supplied to the computerized manufacturing device controls the manufacturing device to synthesize the object, which object has the desired specifically calculated material properties. For example, assume the manufacturing is carried out using a braider for manufacturing a composite material. During the weaving of the composite, by allowing the computer to control the speed of various machine parts, the tightness of the weave is controlled. The tighter the weave, the higher the stiffness (low flexibility). For example, in the case of the prosthetic hip, regions of both high and low stiffness are required. Using the geometric model and the extracted material property coefficients, the manufacturing process and specifically, the tightness of the weave, can be controlled to provide a region of high stiffness (e.g., the region defined by element 601 in FIG. 4) and a region of low stiffness (e.g., the region defined by element 603 in FIG. 4). By appropriately controlling the manufacturing process in accordance the inventive methodology, a prosthetic hip may be produced which responds to applied loads in a manner which is substantially identical to manner in which the human hip would respond to the same applied load. Such a prosthesis can be developed with specific response characteristics for a particular individual.

The above-described methodology is typically carried out as an iterative process. For example, the results of an initial iteration may generally indicate that a fiber composite manufactured using a braider provides the best match to the extracted material property coefficients in the intended application. Thus, in a second subsequent iteration, the finite element model may be modified to take into account the smallest incremental volume that can be controllably braided using a computer-controlled braider. Preferably, each of the elements in the finite element model corresponds to no less than the smallest incremental volume that can be controllably manufactured using the manufacturing technique by which the object is to be manufactured. For example, for a braiding process using a braider, the smallest volume that can be controllably braided is approximately one cubic millimeter. In other words, it is possible to controllably vary a braid pattern to produce an object having material or constitutive properties that vary on the order of a cubic millimeter. This smallest incremental volume will of course vary in accordance with the manufacturing process or technique selected and may, in addition, be dependent on available manufacturing equipment. Thus, although the smallest incremental volume that can be braided by a state-of-the-art braider is one cubic millimeter, it is not necessarily true that all braiders will be capable of such operation. Accordingly, in such cases, the smallest incremental volume is determined by the capabilities of an available braider. It will be appreciated that as manufacturing techniques improve and smaller incremental volumes can be controllably manufactured, the methodology of the instant invention may be utilized with resized or different shaped elements.

The mathematics of the inventive method are valid for other types of manufacturing processes other than composites such as the manufacturing of metals, plastics, and ceramics. The inventive method is also valid for manufacturing objects based on their desired responses to heat and electric currents. In short, the inventive method can be used for any computer controlled manufacturing process, where precision volumetrically controlled manufacturing is desired.

The method of the present invention is particularly useful when increased efficiency of an object is desired. In traditional manufacturing, the emphasis is on precision manufacturing of an object's geometry, without much, if any, control over the internal structural makeup of this geometry. In accordance with inventive methodology, the material matrix is the unknown and an iterative process may be carried out to optimize the material property matrix while keeping the geometry fixed.

Thus, in accordance with the present invention, the input parameters of anyprocess may be precisely varied to create an object with a precisely defined material property matrix. As manufacturing continues to improve, the above-described methodology is applicable even though the smallest incremental volume that can be controllably manufactured may continue to decrease in size.

Figure 6:
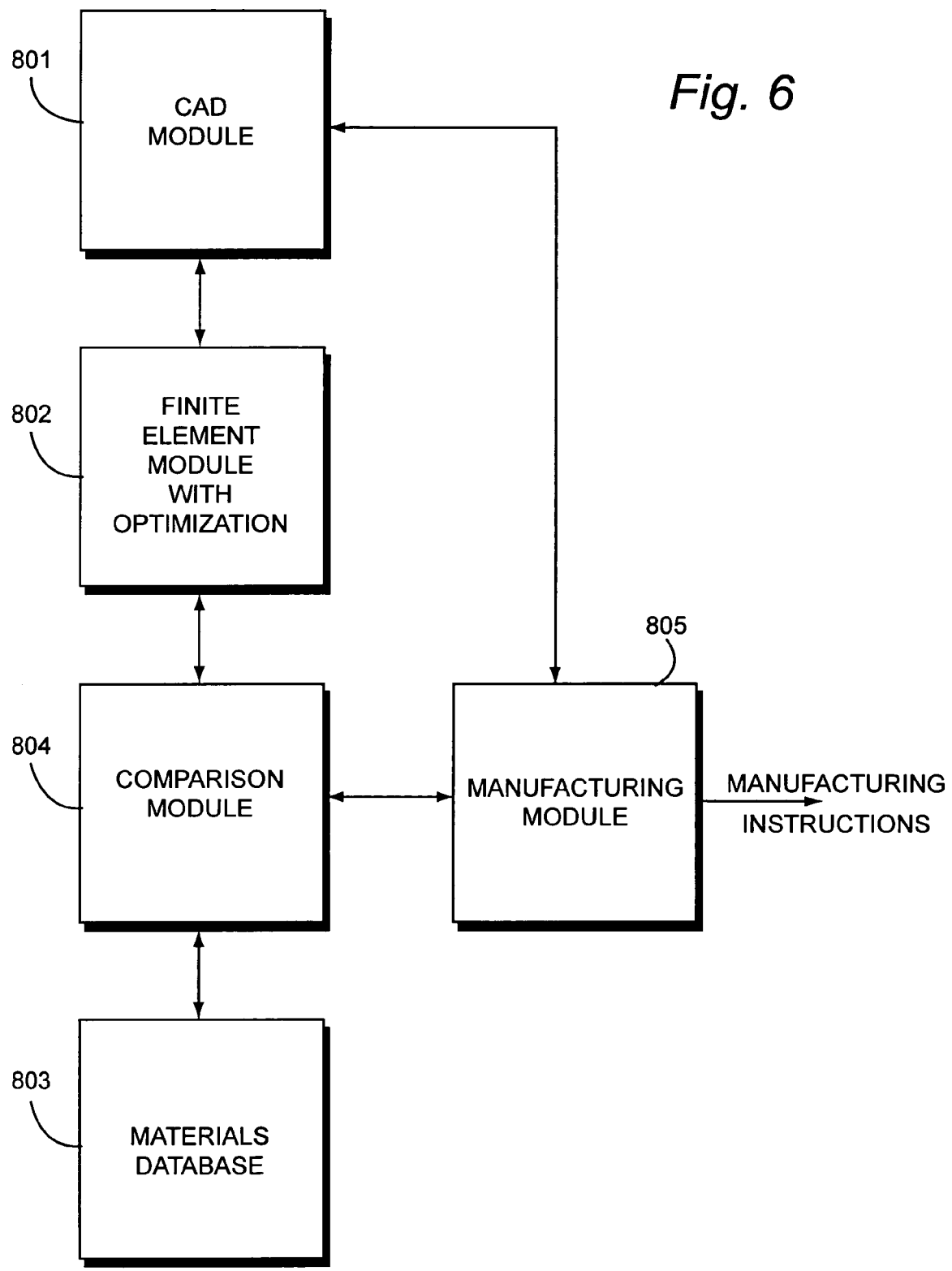
FIG. 6 illustrates functional modules that may be used to implement the present invention.

FIG. 6 illustrates various functional modules that may be used to implement the methodology of the instant invention. A computer-aided design (CAD) module 801 is a three-dimensional graphics software program for generating a geometrical model definition. Such a geometrical model definition includes coordinate points precisely locating the object design in a three-dimensional coordinate system. This may be provided by a graphics software package using, for example, X, Y, and Z coordinate points and appropriate locating vectors where necessary. The three-dimensional graphics software package utilizes appropriate data structures for defining particular points in the database of the graphics program. By utilizing algorithms in the graphics program, other points in the object can be defined and generated. The graphics program preferably utilizes appropriate vector and matrix routines whereby an object can be rotated or otherwise moved in computer memory and can be dimensioned whereby the coordinates for any one point are known with respect to other points. As noted above, suitable CAD software packages include I-DEAS, CATIA, and ANVIL-5000.

A finite element module 802 is used to generate the finite element model of the object from data stored in the graphics program database. Finite element module 802 is a software package for dividing the object designed using computer-aided-design module 801 into a plurality of elements and expressing one or more unknown field variables in terms of assumed approximating functions within each element. Finite element module 802 is programmed to calculate the optimum material properties for each element as discussed above. Suitable software packages for finite element module 802 include NASTRAN, ABAQUS, and ANSYS.

A materials data base module 803 is an archive or archives of material property coefficients with their corresponding manufacturing process and manufacturing-process control parameters. The archives thus correlate the properties of materials to the manufacturing process and manufacturing process parameters used to create the materials.

A comparison module 804 compares the material properties determined using finite element module 802 to the material data in material data base module 803 in order to determine (1) which material has material properties which match or most closely match the material properties determined using finite element module 802 and (2) the manufacturing process and manufacturing process parameters associated with this matched material. Comparison module 804 may be implemented, for example, by a knowledge base having a fact base for storing material property data from finite element module 802 and material property data from material data base module 803 and a rule base containing rules for comparing and matching the material property data from finite element module 802 and the material property data from material data base module 803.

A manufacturing module 805 translates and sequences the manufacturing parameters derived from comparison module 804 to provide manufacturing instructions to a manufacturing machine for manufacturing an object in having the geometry defined using computer-aided-design module 801. The manufacturing of the object may be carried out by a machine suitable for the particular material. For example, metals may be manufactured by reproducing surface geometry (surface points in space), composites may be manufactured by controlling weave configuration and fiber choice, and polymers may be manufactured by chemical choice, temperature, and pressure. Computer assistance in manufacturing allows machines to be quickly adjusted to vary the manufacturing process from one object to the next or within various regions of a single object.

The above-described modules may be provided separately or as an integrated package. The VCM system and process relies on computer processing to assist in the engineering effort. The computer processing is used throughout the design, analysis, and manufacture of a part or assembly. During the design and analysis stages, the system is preferably configured to permit visualization of the sensitivity of mechanical properties such as stress and strain to changes in material properties. This is accomplished by iteratively solving for material properties, subsequently solving for mechanical properties, and displaying both results in close to real time for each iteration. It is then used to determine the optimal material properties per element or group of elements. During manufacturing, the system is used to determine the material makeup such as selection of fiber and composite materials, fiber volume, and fiber orientation.

During pre-processing and post-processing, the system preferably provides a viewing window that displays three-dimensional finite element models with the properties of each element rendered as a different color. This model is displayed as either wireframe, hidden line, or solid. There is also the ability to volumetrically render the results of the finite element analysis. The results, e.g. Young's modulus or Poisson's ratio, for each element is read into the software. The system then interpolates the results throughout each 3-D element and assigns a color value from a spectrum that represents the value range of the desired material property.

This data is then rendered onto the meshed geometry of the finite element model. Transparency values are assigned to the elements to allow for the interior elements to be viewed. The system has the ability to translate from proprietary file formats from CAD/CAM and FEA tools such as ABAQUS, NASTRAN, I-DEAS and Unigraphics as well as standard file formats such as IGES. Many of the files that are exchanged from the different packages are ACSII text files. Translators convert the different text-based files from one form to another, thereby integrating the packages independently from the user.

During the analysis stage, the system controls the exchange of data between the FEA processing to the optimization processing. The results from each iteration may be sent to the postprocessor and viewed almost in real time. The data that is being exchanged is in ASCII format and software code parses the text files and translates the file format into the forms needed by the separate packages. The system preferably includes a GUI that allows the user to manipulate the data. Also the system preferably has the ability to output the results from each iteration to the viewer in real time. This feature not only allows for simulation of "end results" but also "intermediate solutions".

The system also includes a database for storing the composite materials test data. The SQL-based database includes customized queries that allow for the automatic retrieval of the optimal material property values for a part and recommends the optimal manufacturing method and parameters. An object-oriented approach creates a data structure that dynamically allocates memory and allows for swapping of large amounts of data. This method ensures scalability while maintaining a high level of performance.

Figure 7:
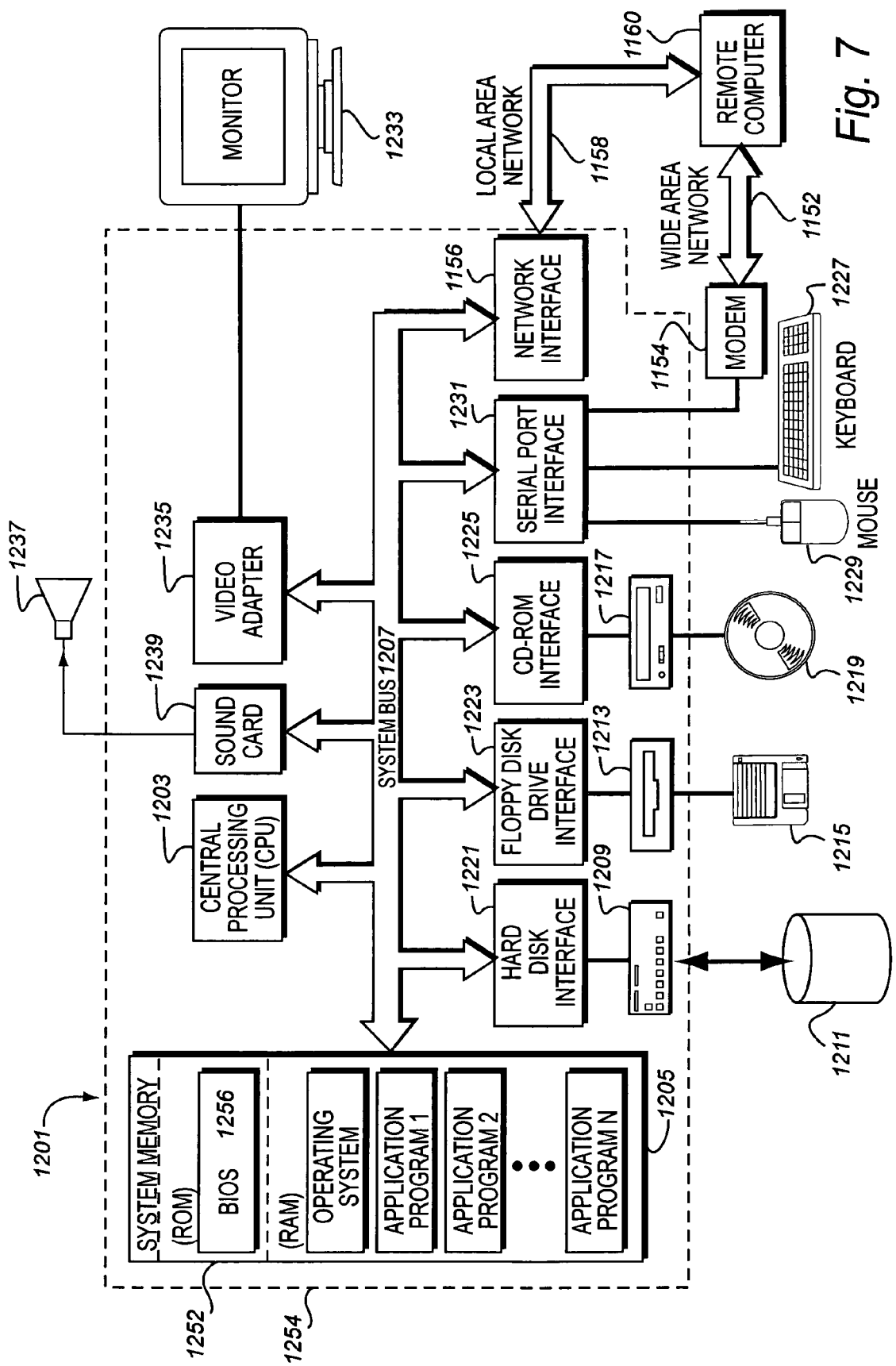
FIG. 7 is a block diagram of an environment which may be used to implement one or more of the functional modules of FIG. 6.

FIG. 7 illustrates computer equipment usable for performing the computer-implemented processes described above. Various ones of the processes may be performed on the same or on different computers. System 1201 includes a processing unit 1203 and a system memory 1205. A system bus 1207 couples various system components including system memory 1205 to processing unit 1203. System bus 1207 may be any of several types of bus structures including a memory bus or memory controller, a peripheral bus, and a local bus using any of a variety of bus architectures. System memory 1207 includes read only memory (ROM) 1252 and random access memory (RAM) 1254. A basic input/output system (BIOS) 1256, containing the basic routines that help to transfer information between elements within computer system 1201, such as during start-up, is stored in the ROM 1252. System 1201 further includes various drives and associated computer-readable media. A hard disk drive 1209 reads from and writes to a (typically fixed) magnetic hard disk 1211. An additional (possible optional) magnetic disk drive 1213 reads from and writes to a removable "floppy" or other magnetic disk 1215. An optical disk drive 1217 reads from and, in some configurations, writes to a removable optical disk 1219 such as a CD ROM or other optical media. Hard disk drive 1209 and optical disk drive 1217 are connected to system bus 1207 by a hard disk drive interface 1221 and an optical drive interface 1225, respectively. The drives and their associated computer-readable media provide nonvolatile storage of computer-readable instructions, data structures, program modules and other data for computer system 1201. In other configurations, other types of computer-readable media that can store data that is accessible by a computer (e.g., magnetic cassettes, flash memory cards, digital video disks, Bernoulli cartridges, random access memories (RAMs), read only memories (ROMs) and the like) may also be used.

A number of program modules may be stored on the hard disk 1211, removable magnetic disk 1215, optical disk 1219 and/or the ROM 1252 and/or the RAM 1254 of system memory 1205. Such program modules may include an operating system providing graphics and sound APIs, one or more application programs, other program modules and program data. A user may enter commands and information into computer system 1201 through input devices such as a keyboard 1227, pointing device 1229, microphones, joysticks, game controllers, satellite dishes, scanners, or the like. These and other input devices can be connected to processing unit 1203 through a serial port interface 1231 that is coupled to system bus 1207, but may be connected by other interfaces, such as a parallel port, Fire wire bus or a universal serial bus (USB). A monitor 1233 or other type of display device is also connected to system bus 1207 via an interface, such as a video adapter 1235.

System 1201 may also include a modem 1154 or other network interface means for establishing communications over a network 1152 such as the Internet. Modem 1154, which may be internal or external, is connected to system bus 123 via serial port interface 1231. A network interface 1156 may also be provided for allowing system 1201 to communicate with a remote computing device 1150 (e.g., another system 1201) via a local area network 1158 (or such communication may be via wide area network 1152 or other communications path such as dial-up or other communications means). System 1201 will typically include other peripheral output devices, such as printers and other standard peripheral devices.

In one example, video adapter 1235 may include a 3D graphics pipeline chip set providing fast 3D graphics rendering in response to 3D graphics commands issued based on a standard 3D graphics application programmer interface such as Microsoft's DirectX 7.0 or other version. A set of stereo loudspeakers 1237 is also connected to system bus 1207 via a sound generating interface such as a conventional "sound card" providing hardware and embedded software support for generating high quality stereophonic sound based on sound commands provided by bus 1207.

Figure 8:
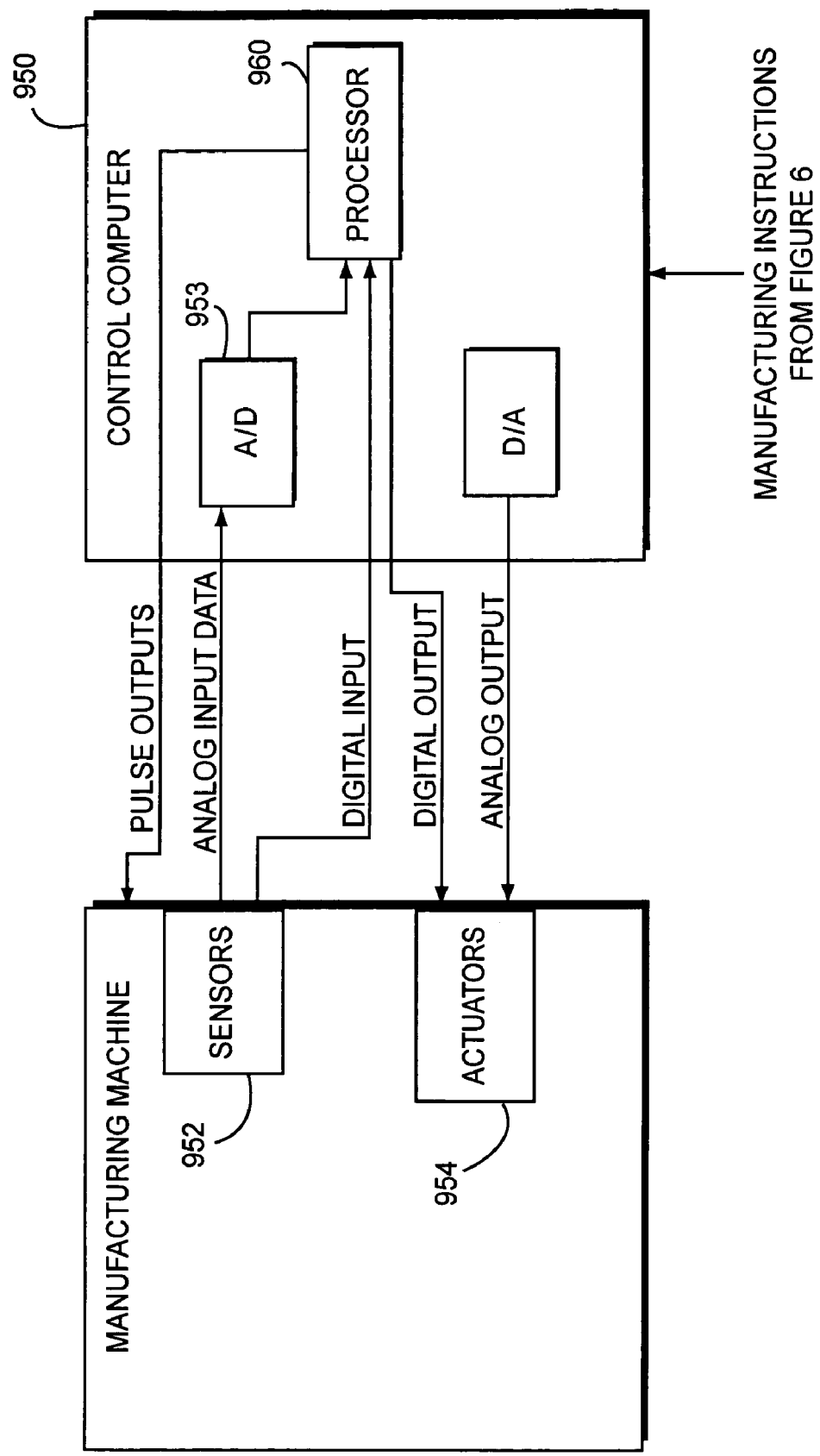
FIG. 8 is a schematic of a control computer for controlling a manufacturing machine.

FIG. 8 is a control computer schematic for a generalized control computer using a control computer 950. The control computer is downloaded with the manufacturing instructions generated by manufacturing module 805 of FIG. 6. Information such as braider bed speed, fiber tension, temperature, pressure, etc. is obtained from sensors 952 of a manufacturing machine in digital format (on/off, open/closed) or analog format (voltage). Analog inputs are converted to a digital representation by analog-to-digital converter 953 of control computer 950. Control computer 950 includes a processor 960 for analyzing the information from sensors 952 and generating signals which are supplied to actuators 954 for adjusting the settings of the manufacturing machine in accordance with the downloaded manufacturing instructions. In addition to analog and digital outputs, pulse outputs may be provided to drive stepping motors, frequently used with machine tools and other equipment. Of course, the specifics of control computer 950 will depend on the manufacturing machine that is utilized. Details of control computers useful in surface manufacturing process may be found, for example, in the above-identified Bedworth text.

As described above, VCM provides the ability to control desired material property characteristics throughout a structure. In essence, VCM enhances the tailorability of conventional composite materials. Instead of controlling properties in the longitudinal and transverse directions of an entire structure by altering the axial direction of individual plies, VCM allows the mechanical, electro-magnetic, and thermal characteristics to be controlled and varied in all three directions to a fidelity of one cubic millimeter. In addition, the manufacturing process is a true three-dimensional structure, not a thickness built-up by stacking two-dimensional plies. Therefore, delamination and shearing between plies are no longer major concerns that drive the design process.

The variation in properties throughout a structure can be accomplished in several ways (e.g., manipulating fiber volume at individual levels, controlling matrix volume, varying fiber/matrix type as it is being fabricated, varying fiber orientation, and varying degree of cure as it is being laid down).

Just as in a conventional composite laminate, altering the fiber volume can vary the properties. VCM can manipulate the fiber volume at the individual fiber level within a structure by altering either the number of fibers or the amount of matrix in an area. Fibers are added to or cut from the bundle as the fiber bundle is being laid in place.

Alternatively, the amount of matrix material being placed with the fiber bundle may be increased or decreased. This matrix control is accomplished in two ways. The first method involves laying down a bi-component fiber. The bi-component fiber is one in which the fiber is sheathed in the matrix material. The thickness of the sheath is controlled as the fiber is being laid, thus giving very specific fiber volume control. The second method uses co-mingled strands of fiber and matrix. Just as the fiber bundles are added to or subtracted from, the quantity of matrix strands are controlled.

Another method of controlling the material properties is to alter the fiber and/or matrix choice throughout the structure as it is being fabricated. This allows for combinations of fibers within the same structure. Adding to and subtracting from the fiber bundle yields a fairly continuous material transition resulting in a seemingly continuous gradient in material properties. For example, a structure fabricated using the VCM process may require carbon fiber to achieve a specific mechanical property. However, only one end of the structure may be subjected to a high tensile load. Conventional methods would use a high-performance carbon prepreg to fabricate the entire structure. Using VCM, however, the structure is fabricated such that a high-performance, high-cost carbon fiber is used throughout the structure, but in a diminishing fiber volume towards the non-load-bearing end. It might be more cost-effective, though, to use the high-performance carbon fiber only at the loaded end. Throughout the remainder of the structure, the high-performance carbon is gradually substituted with a lower-performance carbon fiber that has similar mechanical properties. Conventional composite methods do not perform such a seamless substitution in a cost-effective manner. Another example of the usefulness of this method can be seen in a composite aircraft wing. The outer skin of the wing must be damage tolerant and capable of withstanding small impacts without delamination. The same capability is not required within the wingbox. Thus, for example, a wing that has a high kevlar to carbon ratio on the outer skin to absorb impact may be fabricated. The three-dimensional reinforcement that is integral to the VCM method also assists in arresting delamination after impact. The kevlar is gradually substituted with carbon as the inner sections of the wingbox are fabricated. Again, this method would be more cost-effective than current efforts to fabricate the entire wing out of a carbon/kevlar combination.

As with conventional composite methods, VCM is capable of varying fiber orientation within the structure as it is being fabricated. The difference with VCM is that the fiber orientation is pre-calculated, for optimal material properties, and the fiber is fabricated accordingly in unique finite volumes. Because the VCM method pre-calculates precise fiber orientation, the fiber orientations will be more repeatable and can be more exact than the basic 0, 90, +/−45, +/−60 lay-ups used in conventional composite laminates.

An additional method to tailor the properties of the matrix is to control the degree of cure of the matrix as it is being laid-down. This involves the incorporation of such technology as electron-beam curing, microwave curing and/or focused infrared energy curing.

Once the materials, fiber volumes and cure method are determined, the VCM process can manufacture the structure by one of several methods.

One method is through the customization of rapid prototyping technology. Currently, RP techniques such as Fused Deposition Molding (FDM) are used only to build proof-of-concept parts, not production parts. For this reason, the materials used by this equipment are limited to wax and non-engineering plastics. With some modification, rapid prototyping equipment can be used to lay thermoplastics, reinforcing fibers, epoxies, and the like to create production parts, not just prototype models.

Equipment can also be modified to lay several types of materials at once, down to individual fibers. The machinery can be provided with the ability to create bi-component fibers as they are being laid into the structure. Commercial FDM equipment already has the control and accuracy required by VCM to vary material properties on the scale of one cubic millimeter.

Another manufacturing method is braiding. Braiding is just beginning to make its foray into the commercial sector. Research and industry surveys indicate that the process is limited to braiding dry fibers that are then infused with resin. However, if the braiding process is coupled with bi-component fibers or co-mingled yarns, then the infusion process, which is not very consistent, becomes unnecessary. In addition, the infusion process does not allow for specific control of fiber volume. Braiding the matrix with the fiber would allow such control. The braiding process also lends itself well to further development because it can be used to yield a true three-dimensional reinforcement.

Any application, patent, technical document, textbook, or other publication cited herein should be construed to be incorporated by reference as to any subject matter deemed essential to the present disclosure.

While various embodiments of the present invention have been described above, it should be understood that they have been presented by way of example, and not limitation. Thus, the breadth and scope of the present invention should not be limited by any of the above-described exemplary embodiments, but should be defined only in accordance with the following claims and their equivalents.

I claim:

1. A method for manufacturing an object having a potential $\{x\}$ that is generated in response to a field $\{f\}$ applied thereto, the method comprising:

generating a computerized mathematical model of the object by discretizing a geometric model of the object into a plurality of finite elements and specifying values for the field $\{f\}$ and potential $\{x\}$ relative to the finite elements;

calculating a material property matrix [k] based on the field $\{f\}$ and the potential $\{x\}$;

extracting material property coefficients from the material property matrix [k] for each finite element in the computerized mathematical model;

comparing the extracted material property coefficients to material property coefficients for known materials to match the extracted material property coefficients to the material property coefficients for known materials;

determining manufacturing equipment control parameters for each volume increment of the object based on the matched material property coefficients;

controlling the manufacturing equipment in accordance with the determined manufacturing equipment control parameters to thereby manufacture the object, wherein, if the matched material property coefficients correspond to a composite material, the manufacturing equipment control parameters comprises parameters for controlling composite manufacturing equipment and the controlling of the manufacturing equipment comprises controlling composite manufacturing equipment, and wherein the composite material comprises structural fibers laminated in a resin matrix into which an impurity is introduced, the amount of the impurity introduced into the resin matrix being controllably variable for the respective volume increments of the object.

2. The method according to claim 1, further comprising: specifying that the material properties of the finite elements have a particular symmetry.

3. The method according to claim 2, wherein the material properties of the finite elements are specified to be isotropic.

4. The method according to claim 2, wherein the material properties of the finite elements are specified to be transversely isotropic.

5. The method according to claim 1, wherein the generating of a computerized mathematical model of the object further includes determining the smallest volume increment that can be manufactured using the manufacturing equipment.

6. The method according to claim 1, wherein the field $\{f\}$ is a mechanical force field and the potential $\{x\}$ is a displacement.

7. The method according to claim 1, wherein the field $\{f\}$ is an electric current field and the potential $\{x\}$ is a voltage.

8. The method according to claim 1, wherein the field $\{f\}$ is a magnetic field and the potential $\{x\}$ is a magnetic vector potential.

9. The method according to claim 1, wherein the field $\{f\}$ is a thermal flux field and the potential $\{x\}$ is a temperature.

10. The method according to claim 1, wherein the field $\{f\}$ is a fluid velocity field and the potential $\{x\}$ is a fluid potential.

11. The method according to claim 1, wherein the impurity comprises biologic material.

12. The method according to claim 1, wherein the impurity comprises bone.

13. The method according to claim 1, wherein the impurity comprises crushed bone.

14. The method according to claim 1, wherein the impurity comprises co-factors.

15. The method according to claim 1, wherein the impurity comprises biological cells.

16. The method according to claim 1, wherein the impurity comprises bio-active materials.

17. The method according to claim 1, wherein the impurity comprises medications.

18. The method according to claim 1, wherein the impurity comprises antibiotics.

19. The method according to claim 1, wherein the impurity comprises radioactive materials.

20. The method according to claim 1, wherein the object being manufactured is a prosthetic implant for replacing a body part and the field $\{f\}$ and potential $\{x\}$ are specified based on the in vivo forces applied to the body part to be replaced and the in vivo displacements generated in the body part to be replaced when the forces are applied thereto.

21. An object made in accordance with the method of claim 1, wherein the object is selected from the group consisting of an automobile part, an aircraft part, a prosthetic implant, a golf club shaft, a tennis racket, a bicycle frame, and a fishing pole, and wherein different portions of the object have different material properties corresponding to the matched extracted material property coefficients for known materials.

22. A computer-implemented method for determining machine control instructions for manufacturing an object having a potential $\{x\}$ that is generated in response to a field $\{f\}$ applied thereto, the method comprising:

generating a computerized mathematical model of the object by discretizing a geometric model of the object into a plurality of finite elements and specifying values of the field $\{f\}$ and potential $\{x\}$ relative to the finite elements;

calculating a material property matrix [k] based on the field $\{f\}$ and potential $\{x\}$;

extracting material property coefficients from the material property matrix [k] for each finite element in the computerized mathematical model;

comparing the extracted material property coefficients to material property coefficients for known materials to match the extracted material property coefficients to the material property coefficients for known materials;

determining manufacturing equipment control parameters for each volume increment of the object based on the matched material property coefficients; and generating machine control instructions for controlling the manufacturing equipment in accordance with the manufacturing equipment control parameters to manufacture the object, wherein, if the matched material property coefficients correspond to a composite material, the manufacturing equipment control parameters comprise parameters for controlling composite manufacturing equipment and the machine control instructions comprise instructions for controlling the composite manufacturing equipment, and wherein the composite material comprises structural fibers laminated in a resin matrix into which an impurity is introduced, the amount of the impurity introduced into the resin matrix being controllably variable for the respective volume increments of the object.

23. The method according to claim 22, wherein the object being manufactured is a prosthetic implant for replacing a body part and the field $\{f\}$ and potential $\{x\}$ are specified based on the in vivo forces applied to the body part to be replaced and the in vivo displacements generated in the body part to be replaced when the forces are applied thereto.

24. The method according to claim 22, wherein the impurity comprises biologic material.

25. The method according to claim 22, wherein the impurity comprises bone.

26. The method according to claim 22, wherein the impurity comprises crushed bone.

27. The method according to claim 22, wherein the impurity comprises co-factors.

28. The method according to claim 22, wherein the impurity comprises biological cells.

29. The method according to claim 22, wherein the impurity comprises bio-active materials.

30. The method according to claim 22, wherein the impurity comprises medications.

31. The method according to claim 22, wherein the impurity comprises antibiotics.

32. The method according to claim 22, wherein the impurity comprises radioactive materials.

33. A computer system programmed to perform the method of claim 22.

34. A control system programmed with machine control instructions for controlling composite manufacturing equipment to manufacture the composite object, wherein the machine control instructions are generated in accordance with the method of claim 22.

35. Composite manufacturing equipment comprising a control system programmed with machine control instructions for controlling the composite manufacturing equipment to manufacture the composite object, wherein the machine control instructions are generated in accordance with the method of claim 22.

36. A method for manufacturing an object for which a defined field $\{f\}$ generates a potential $\{x\}$ in response thereto, the method comprising:
  (1) generating a computerized mathematical model of the object by discretizing a geometric model of the object into a plurality of finite elements;
  (2) specifying values of the field $\{f\}$ and the potential $\{x\}$ relative to the finite elements;
  (3) calculating a material property matrix [k] based on the field $\{f\}$ and the potential $\{x\}$, wherein the material property matrix [k] comprises a plurality of values each corresponding to one or more material property coefficients;
  (4) comparing each of the plurality of values in the material property matrix [k] to known material properties and, responsive to a match, selecting a corresponding manufacturing process parameter for a volume increment of the object, wherein the selected manufacturing process parameter is usable for controlling composite manufacturing equipment if the matched known material property is a material property for a composite material;
  (5) controlling the composite manufacturing equipment in accordance with the selected manufacturing process parameters to thereby manufacture the object,
  wherein the composite material comprises structural fibers laminated in a resin matrix into which an impurity is introduced, the amount of the impurity introduced into the resin matrix being controllably variable for the respective volume increments of the object.

37. The method according to claim 36, wherein the object being manufactured is a prosthetic implant for replacing a body part and the field $\{f\}$ and potential $\{x\}$ are specified based on the in vivo forces applied to the body part to be replaced and the in vivo displacements generated in the body part to be replaced when the forces are applied thereto.

38. The method according to claim 36, wherein the impurity is selected from the group consisting of: biologic materials, bone, crushed bone, co-factors, biological cells, bio-active material, medications, antibiotics, and radioactive materials.

* * * * *